United States Patent [19]

Brooks et al.

[11] Patent Number: 5,026,729
[45] Date of Patent: Jun. 25, 1991

[54] LIPOXYGENASE INHIBITING COMPOUNDS

[75] Inventors: Dee W. Brooks; James B. Summers, both of Libertyville; James H. Holms, Gurnee, all of Ill.

[73] Assignee: Abbott Laboratories, Abbott Park, Ill.

[21] Appl. No.: 430,841

[22] Filed: Nov. 2, 1989

Related U.S. Application Data

[63] Continuation-in-part of Ser. No. 12,978, Feb. 10, 1987, Pat. No. 4,897,422.

[51] Int. Cl.$^5$ .................. A61K 31/17; A61K 31/185; C07C 259/00
[52] U.S. Cl. .................................. 514/575; 562/621; 562/623
[58] Field of Search ................. 562/623, 621; 514/575

[56] References Cited

U.S. PATENT DOCUMENTS

| | | | |
|---|---|---|---|
| 3,890,377 | 6/1975 | Marshall | 260/550.5 H |
| 4,604,407 | 8/1986 | Haslanger | 514/575 |
| 4,738,986 | 4/1989 | Kneen et al. | 514/575 |

Primary Examiner—J. E. Evans
Attorney, Agent, or Firm—Jerry F. Janssen; Steven F. Weinstock

[57] ABSTRACT

Compounds having 5- and 12-lipoxygenase inhibitory activity have the structure

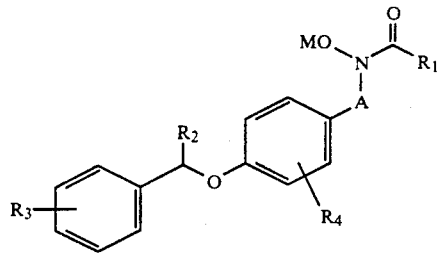

where A is straight or branched divalent alkylene of from one to four carbon atoms, $R_1$ is methyl, amino, or alkylamino of from one to six carbon atoms and the substituent group $R_2$ is $C_1$–$C_2$ alkyl.

The group $R_3$ is one or more substituents selected from hydrogen, alkyl of from one to six carbon atoms, alkoxy of from one to six carbon atoms, thioalkoxy of from one to six carbon atoms, halogen, cyano, and trihalomethyl, and $R_4$ is one or more substituents selected from hydrogen, alkyl of from one to six carbon atoms, alkoxy of from one to six carbon atoms, thioalkoxy of from one to six carbon atoms, hydroxy, halogen, cyano, and trihalomethyl, with the proviso that when $R_1$ is amino and A is >CHCH$_3$, $R_3$ and $R_4$ may not both be hydrogen.

The group designated M is hydrogen, a pharmaceutically acceptable cation, or a metabolically cleavable group. Pharmaceutical compositions and a method of inhibiting 5- and 12-lipoxygenase activity are also disclosed.

6 Claims, No Drawings

LIPOXYGENASE INHIBITING COMPOUNDS

CROSS-REFERENCE TO RELATED APPLICATIONS

This application is a continuation-in-part of U.S. Ser. No. 012,978 filed 10 Feb. 1987, now U.S. Pat. No. 4,897,422.

TECHNICAL FIELD

This invention relates to organic compounds having pharmacological activity, to pharmaceutical compositions containing these compounds, and to a method of treating disease states. More particularly, this invention concerns certain organic compounds which inhibit lipoxygenase enzymes, to pharmaceutical compositions containing these compounds, and to methods of inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LT's).

Similarly, 12- and 15-lipoxygenase convert arachidonic acid to 12- and 15-HPETE, respectively. The biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in a number of disease states. For example, the leukotrienes $LTC_4$ and $LTD_4$ are potent constrictors of human airways in vitro, and aerosol administration of these substances to nonasthmatic volunteers induces broncho-constriction. $LTB_4$ and 5-HETE are potent chemotactic factors for inflammatory cells such as polymorphonuclear leukocytes. They also have been found in the synovial fluid of patients suffering from rheumatoid arthritis. Leukotrienes have also been implicated as important mediators in allergic rhinitis, psoriasis, adult respiratory distress syndrome, Crohn's disease, endotoxin shock, and ischemia-induced myocardial injury, among others. The biological activity of the leukotrienes has been reviewed by Lewis and Austeen, *J. Clinical Invest.* 73: 89 (1984) and by J. Sirois, *Adv. Lioid Res.* 21: 78 (1985).

The product, 12-HETE, has been found in high levels in the epidermal tissue of patients with psoriasis. The lipoxins have recently been shown to stimulate elastase and superoxide ion release from neutrophils.

Thus, the lipoxygenase enzymes are believed to play and important part in the biosynthesis of mediators of asthma, allergy, arthritis, psoriasis, and inflammation. Blocking these enzymes interrupts the biochemical pathways believed to be involved in these disease states.

One of the problems associated with the development of compounds which inhibit lipoxygenase is that many such compounds are poorly absorbed into the blood stream if administered orally. Thus, it is difficult to achieve high blood plasma levels of these drugs. Another deficiency of many lipoxygenase inhibitors is that, even when they are absorbed into the blood stream, they are often metabolized and do not have long plasma lifetimes. Metabolic processes convert the compounds into metabolites which are believed to have little or no lipoxygenase inhibitory action. Thus, there is a need for the development of lipoxygenase inhibiting compounds which are readily absorbed into the blood stream with attendant high blood plasma levels, and which have long plasma lifetimes.

SUMMARY AND DETAILED DESCRIPTION OF THE INVENTION

The lipoxygenase inhibiting compounds of the present invention are absorbed well into the blood stream, achieve unexpected blood plasma levels, and have extended half lives. The compounds have the structural formula:

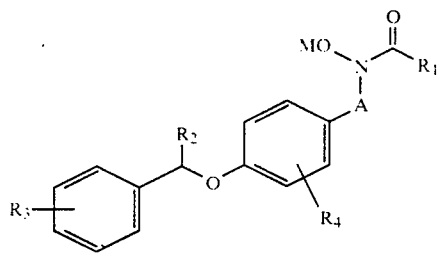

where A is straight or branched divalent alkylene of from one to four carbon atoms, $R_1$ is methyl, amino, or alkylamino of from one to six carbon atoms and the substituent group $R_2$ is $C_1-C_2$ alkyl.

The group $R_3$ is one or more substituents selected from hydrogen, alkyl of from one to six carbon atoms, alkoxy of from one to six carbon atoms, thioalkoxy of from one to six carbon atoms, halogen, cyano, and trihalomethyl, and $R_4$ is one or more substituents selected from hydrogen, alkyl of from one to six carbon atoms, alkoxy of from one to six carbon atoms, thioalkoxy of from one to six carbon atoms, hydroxy, halogen, cyano, and trihalomethyl, with the proviso that when $R_1$ is amino and A is $>CHCH_3$, $R_3$ and $R_4$ may not both be hydrogen.

The group designated M is hydrogen, a pharmaceutically acceptable cation, or a metabolically cleavable group.

In accordance with another embodiment of the present invention, there are provided pharmaceutical compositions for use in inhibiting 5- and 12-lipoxygenase activity in mammals comprising a compound of the present invention as described above, combined in a lipoxygenase-inhibiting effective amount with a pharmaceutically acceptable carrier.

In accordance with a further embodiment of the present invention, there is provided a method of inhibiting 5-and/or 12-lipoxygenase activity in a mammal in need of such treatment by administering to such mammal a pharmaceutical composition of the present invention as described above in an amount effective to inhibit such activity.

Disease states which may be treated in humans or lower animal hosts by the compounds, compositions and methods of this invention as described above include, but are not limited to, asthma, rheumatoid arthritis, gout, psoriasis, allergic rhinitis, adult respiratory distress syndrome, Crohn's disease, endotoxin shock, allergic dermatitis, acne, inflammatory diseases of the skin, atherosclerosis, and/or ischemia-induced myocardial injury.

The term "alkyl" as used throughout this specification and appended claims means a straight chain or branched chain saturated monovalent hydrocarbon radical including, but not limited to, methyl, ethyl, n-propyl, iso-propyl, n-butyl, sec-butyl, iso-butyl, tert-butyl, and the like.

The term "alkoxy" denotes an alkyl group as just defined, connected through an oxygen atom to the parent molecular residue.

The term "alkoyl" denotes an alkyl group as defined above, connected through a carbonyl group to the parent molecular residue. Examples include, but are not limited to formyl, acetyl, propionyl, butyryl, iso-butyryl, pivaloyl, and the like.

The term "aroyl" means a substituted or unsubstituted aromatic group such as phenyl, 1- or 2-naphthyl and the like, attached to the parent molecular residue through a carbonyl group.

The terms "halo" and "halogen" denote monovalent radicals derived from fluorine, chlorine, bromine, and iodine.

The terms "pharmaceutically acceptable cation" refers to non-toxic cations including, but not limited to, those derived from the alkali and alkaline earth metals such as lithium, sodium, potassium, calcium, magnesium, and the like, as well as non-toxic ammonium, quaternary ammonium, and amine cations including, but not limited to, ammonium, tetramethylammonium, tetraethylammonium, methylamine, ethylamine, dimethylamine, trimethylamine, triethylamine, and the like.

The term "metabolically cleavable group" is used herein to mean a moiety which is readily cleaved in vivo from the compound bearing it, which compound, after cleavage remains or becomes biologically active. Metabolically cleavable groups include such groups as alkoyl and substituted and unsubstituted aroyl as represented by, but are not limited to, acetyl, ethoxycarbonyl, methoxycarbonyl, tert-butoxycarbonyl, glutaryl, succinyl, carbamoyl, and the like. Because of the ease with which the metabolically cleavable groups of the compounds of this invention are removed in vivo, the compounds bearing such metabolically cleavable groups may act as prodrugs of other lipoxygenase inhibitors. Such compounds therefore have the advantage that they may exhibit improved bioavailability as a result of enhanced solubility and/or rate of absorption into the host organism.

Although the group A in the generic structural formula given above may be straight or branched divalent alkylene of from one to four carbon atoms, preferred compounds of the present invention are those in which A is an ethyl group in which both of the remaining portions of the molecule are attached to the same carbon atom; i.e., compounds in which A is the divalent radical >CHCH$_3$. Also preferred are compounds of the present invention in which either or both of the substituent groups R$_3$ and R$_4$ are alkyl of from one to six carbon atoms, particularly methyl.

Examples of compounds falling within the scope of the present invention include, but are not limited to the following:

N-hydroxy-N-[1-(4-(1-phenylethoxy)-3,5-dimethoxyphenyl)ethyl]urea;

N-hydroxy-N-[1-(4-(1-phenylethoxy)-3-methylphenyl)ethyl]urea;

N-hydroxy-N-[1-(4-(1-phenylethoxy)-2-methylphenyl)ethyl]urea;

N-hydroxy-N-[1-(4-(1-phenylethoxy)-2-hydroxyphenyl)-ethyl]urea;

N-hydroxy-N-[1-(4-(1-phenylethoxy)-3-methoxyphenyl)-ethyl]urea;

N-hydroxy-N-[1-(4-(1-(2-methylphenyl)ethoxy)-phenyl)-ethyl]urea;

N-hydroxy-N-[1-(4-(1-phenylethoxy)phenyl)ethyl]-N'-methylurea;

N-hydroxy-N-[1-(4-(1-phenylethoxy)phenyl)ethyl]-N'-propylurea;

N-hydroxy-N-[1-(4-(1-phenylethoxy)phenyl)-2-methylpropyl]urea;

N-hydroxy-N-[1-(4-(1-phenylethoxy)phenyl)butyl]urea;

N-hydroxy-N-[1-(4-(1-phenylethoxy)-2-methoxyphenyl)ethyl]

N-hydroxy-N-[1-(4-(1-phenylethoxy)-2-hydroxy-3-methylphenyl)ethyl]urea;

N-hydroxy-N-[1-(4-(1-phenylethoxy)-3,5-dimethylphenyl)-ethyl]urea;

N-hydroxy-N-[1-(4-(1-phenylethoxy)-3-chlorophenyl)-ethyl]urea;

N-hydroxy-N-[!-(4-(1-phenylethoxy)-2-iso-propyloxyphenyl)-ethyl]urea;

N-hydroxy-N-[1-(4-(1-phenylethoxy)-3-cyanophenyl)-ethyl]urea;

N-hydroxy-N-[1-(4-(1-(4-fluorophenyl)ethoxy)-3-cyanophenyl)-ethyl]urea;

N-hydroxy-N-[1-(4-(1-phenylethoxy)-3,5-dichlorophenyl)-ethyl]urea;

N-hydroxy-N-[1-(4-(1-(4-fluorophenyl)ethoxy)-3-fluorophenyl)ethyl]urea;

N-hydroxy-N-[1-(4-(1-(4-ethylphenyl)ethoxy)-3-fluorophenyl)ethyl]urea;

N-hydroxy-N-[1-(4-(1-(4-fluorophenyl)ethoxy)-2-hydroxy-3-methylphenyl)ethyl]urea;

N-hydroxy-N-[1-(4-(1-(4-cyanophenyl)ethoxy)-phenyl)-ethyl]urea;

N-hydroxy-N-[1-(-4-(1-(4-trifluoromethylphenyl)ethoxy)-3-methylphenyl)ethyl]urea;

N-hydroxy-N-[1-(4-(1-(4-methoxy-3-fluorophenyl)-ethoxy)phenyl)ethyl]urea;

N-hydroxy-N-[1-(4ethoxy)phenyl)-ethyl]urea;

N-hydroxy-N-[1-(4-(1-(3-chlorophenyl)ethoxy)-3-methylphenyl)ethyl]urea;

N-hydroxy-N-[1-(4-(1-(2-chlorophenyl)ethoxy)-3-methylphenyl)ethyl]urea;

N-hydroxy-N-[1-(4-(1-(4-propylphenyl)ethoxy)-3-methylphenyl)ethyl) urea;

N-hydroxy-N-[1-(4-(1-(4-propylphenyl)ethoxy)-phenyl)ethyl]urea;

N-hydroxy-N-[1-(4-(1-(4-fluorophenyl)ethoxy)phenyl)ethyl]-acetamide;

N-hydroxy-N-[1-(4-(1-(4-fluorphenyl)ethoxy)phenyl)ethyl]urea;

N-hydroxy-N-[1-(4-(1-(4-chlorophenyl)ethoxy)phenyl)ethyl]-acetamide; and

N-hydroxy-N-[1-(4-(1-(4-chlorophenyl)ethoxy)phenyl)ethyl]-urea.

METHOD OF TREATMENT

This invention further provides a method of treatment of inhibiting 5- or 12-lipoxygenase activity in a human or lower animal host in need of such treatment, which method comprises administering to a human or lower animal host a compound as previously described in an amount which is effective to inhibit lipoxygenase activity in the host.

The compounds of the present invention may be administered orally, parenterally, or topically in unit dosage formulations which also contain conventional, nontoxic pharmaceutically acceptable carriers, adjuvants, and vehicles, as desired.

The term "parenteral" as used herein includes modes of administration including subcutaneous, intravenous, or intraarterial injection or infusion. The term "topically" encompasses modes of administration including rectally, by inhalation spray, as well as by the more common routes of the skin and mucous membranes of the nose and mouth.

The total daily dose of the compounds of this invention, administered to a host in a single or divided multiple doses, may be in amounts, for example of from about 0.001 to about 100 mg/kg of body weight daily, and more usually from about 0.01 to about 50 mg/kg of body weight per day. Dosage unit compositions may contain such amounts of such submultiples thereof as may be used to make up the total daily dose. It will be understood by those skilled in the art, however, that the specific dose level for any particular patient will depend upon a number of factors including age, body weight, general health, sex, diet, time and route of administration, rates of absorption and excretion, combination with other drugs, if any, and the severity of the condition being treated.

FORMULATION OF THE PHARMACEUTICAL COMPOSITIONS

This invention also provides for compositions in unit dosage form for the inhibition of 5- or 12-lipoxygenase activity in a human or lower animal host in need of such treatment, comprising a compound of this invention as described above in combination with one or more nontoxic pharmaceutically acceptable carriers, adjuvants, or vehicles. The amount of active ingredient that may be combined with such materials to produce a single dosage form will vary, depending upon the factors enumerated above.

A variety of materials can be used as carriers, adjuvants, and vehicles in the pharmaceutical compositions of this invention, which are well known to those skill in the art of pharmaceutical formulation. Injectable preparations such as oleaginous solutions, suspensions, or emulsions, may be formulated using suitable known dispersing or wetting, and suspending agents, as needed. The sterile injectable preparation may employ a nontoxic, non-pyrogenic diluent or solvent such as, for example, sterile water or 1,3-butanediol. Among other acceptable vehicles and solvents that may be employed are sterile 5% dextrose solution, sterile Ringer's solution, and isotonic sodium chloride solution (as described in the United States Pharmacopeia and the National Formulary. In addition, sterile, fixed oils are conventionally employed as solvents or suspending media. For this purpose, any bland fixed oil may be used including synthetic mono-, di- or triglycerides. Fatty acids such as oleic acid can also be used in the preparation of injectable compositions.

Suppositories for rectal administration of the compounds of this invention can be prepared by mixing the active compound with a suitable non-irritating excipient such as cocoa butter or polyethylene glycols which are solid at ordinary temperatures but are liquid at body temperature and which, therefore, melt in the rectum and release the active compound.

Solid dosage forms for oral administration of the compounds of this invention include capsules, tablets, pills, troches, lozenges, powders, and granules. In solid dosage forms, the active compound may be mixed with at least one inert diluent such as lactose, sucrose, or starch. Such dosage forms may also comprise, as is the normal practice, pharmaceutical adjuvants such as stearate lubricants. In the case of capsules, tablets and pills, the dosage forms may also comprise buffering agents. Solid oral preparations can also be prepared with enteric or other coatings which modulate release the active ingredients.

Liquid dosage forms for oral administration include emulsions, solutions, suspensions, syrups, and elixirs containing pharmaceutically acceptable inert diluents commonly used in the art such as water and alcohol. Such compositions may also comprise adjuvants such as wetting agents, emulsifiers, suspending agents, sweeteners, and flavoring and perfuming agents.

SYNTHESIS OF THE COMPOUNDS OF THIS INVENTION

The compounds of the present invention are prepared according to the reactions shown in the Reaction Sequences set out below which exemplify the production of compounds according to the present invention where A is >CHCH$_3$. Referring to Reaction Sequence 1, the desired substituted 1-haloethyl- (where R$_2$ is methyl) or 1-halopropylbenzenes (where R$_2$ is ethyl), 1, is reacted with a substituted 4-hydroxyacetophenone, 2, to produce the corresponding substituted 1-(4-(1-phenylethoxy)phenyl)ethyl acetophenone, 3. The reaction is carried out in a suitable polar, unreactive solvent such as dimethyl sulfoxide or acetone in the presence of a base such as potassium tert-butoxide or potassium carbonate. The resulting substituted acetophenone, 3, is converted to the corresponding oxime, 4, by reaction with hydroxylamine hydrochloride in pyridine/ethanol. The oxime is reduced by the action of a suitable reagent such as sodium cyanoborohydride or borane/amine complexes including the borane/dimethylamine or borane/pyridine complexes to produce the hydroxylamine compound 5.

REACTION SEQUENCE 1

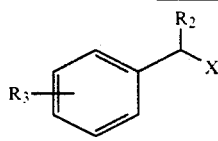

1 X = Cl, Br

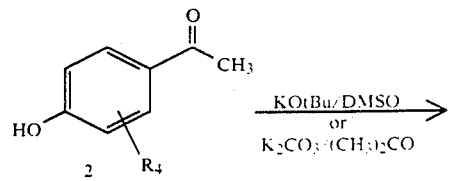

-continued
REACTION SEQUENCE 1

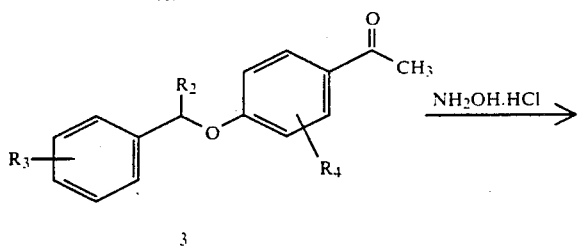

3

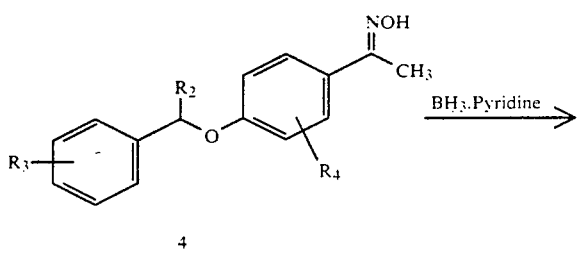

4

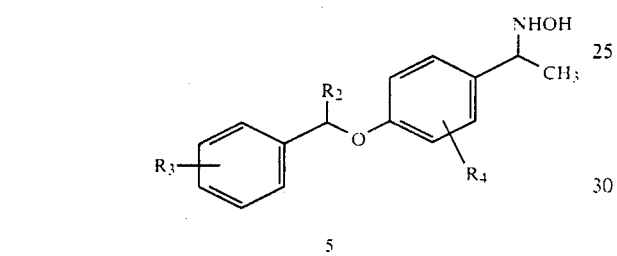

5

The general synthetic method for preparing compounds of the present invention where $R_1$ is methyl is shown in Reaction Sequence 2. The hydroxylamine, 5, prepared in accordance with the methods depicted in Reaction Sequence 1, is reacted first with acetyl chloride/triethylamine to product the N,O-diacetyl derivative 6, and then with lithium hydroxide to provide the desired N-hydroxyacetamide, 7.

REACTION SEQUENCE 2

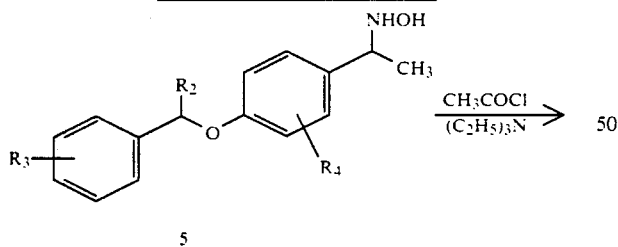

5

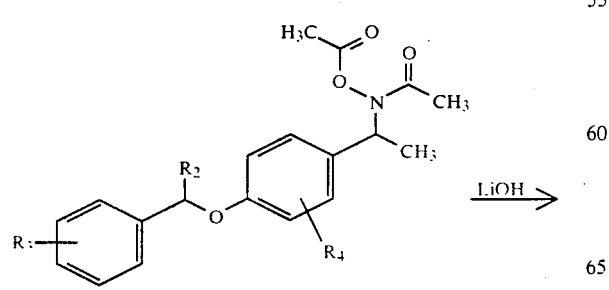

6

-continued
REACTION SEQUENCE 2

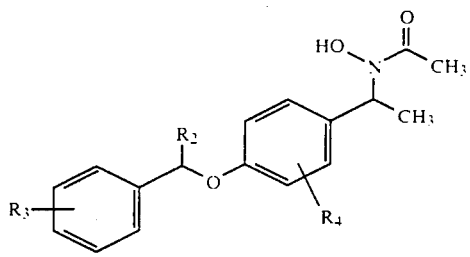

7

Compounds of the present invention in which $R_1$ is amino or alkylamino are produced as shown in Reaction Sequence 3 by reacting the hydroxylamine 5 with gaseous hydrogen chloride followed by phosgene. The resulting carbamoyl chloride, 8, is reacted without isolation with an alkylamine or with aqueous ammonia to produce the urea compounds, 9a or 9b.

REACTION SEQUENCE 3

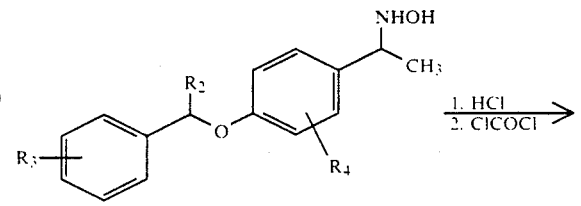

5

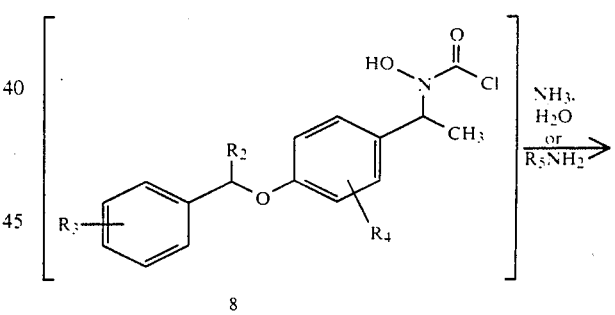

8

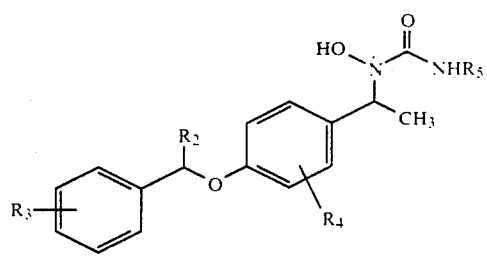

9a. $R_5$ = H
9b. $R_5$ = alkyl

Alternatively, the compounds where $R_1$ is amino can be prepared by reacting the hydroxylamine, 5, with trimethylsilyl isocyanate in a suitable solvent such as tetrahydrofuran followed by workup with ammonium chloride.

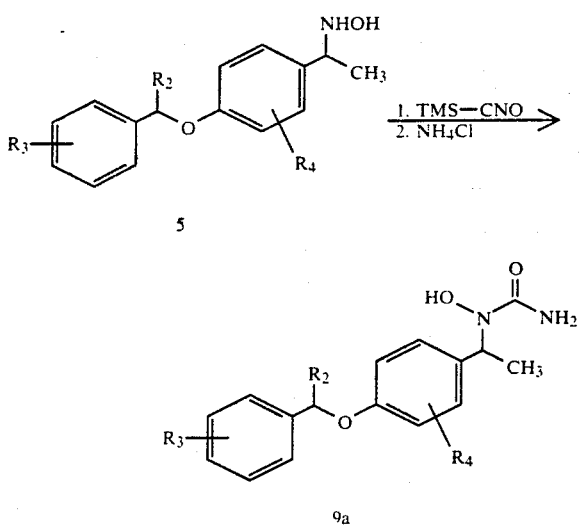

The N-hydroxyl group of the compounds of this invention is capable of forming salts with strong bases. Pharamceutically acceptable salts of these compounds can be formed with appropriate, non-toxic pharmaceutically acceptable cations. Compounds of the present invention where M is a metal cation are produced by reacting the corresponding compound where M is hydrogen with a suitable strong base in tetrahydrofuran (THF). The product salt is then precipitated from the reaction mixture by the addition of hexane and collected by filtration. The sodium salts are produced by reaction of the parent compound with sodium bis-(trimethylsilyl)amide in THF. The potassium salts may be similarly produced by reaction of the parent compounds with potassium bis-(trimethylsilyl)amide in THF. The magnesium salts are prepared by reaction of the parent compounds with a suitable Grignard reagent such as a magnesium alkyl halide in THF. The calcium salts are prepared by reaction of the parent compound in THF with calcium hydride.

Compounds of the present invention in which M is hydrogen may similarly be converted to derivatives or prodrugs in which the group M is a metabolically cleavable group such as formyl, acetyl, propionyl, ethoxycarbonyl, methoxycarbonyl, tert-butoxycarbonyl, glutaryl, succinyl, carbamoyl, and the like. The derivatives or prodrugs are prepared by reacting the parent compounds where M is hydrogen with the appropriate reagent. For example, compounds in which M is acetyl are prepared by reacting the parent compounds in which M is hydrogen with acetic anhydride in THF in the presences of a suitable base such as triethylamine. Substitution of other acid anhydrides such as glutaryl anhydride, succinyl anhydride, and the like produces the corresponding derivatives.

Reaction in THF of the parent compounds where M is hydrogen with acyl chlorides such as acetyl chloride, propionyl chloride, benzoyl chloride, naphthoyl chloride or substituted benzoyl chlorides or naphthoyl chlorides and the like in the presence of an acid scavenger such as triethylamine yields the compounds where M is aroyl or alkoyl. Reaction of the parent compounds where M is hydrogen with compounds such as ethyl chloroformate and the like converts the parent compounds where M is hydrogen into derivatives in which M is —COO(alkyl).

The following examples are provided to enable one skilled in the art to practice the present invention. However, these examples are merely illustrative not to be read as limiting the scope of the invention as it is defined by the appended claims.

EXAMPLE 1

Preparation of N-hydroxy-(1-(4-(1-phenylethoxy)phenyl)-ethyl]urea a) 1-(4-(1-phenylethoxy)phenyl)ethyl acetophenone was prepared by adding sodium tert-butoxide (2.84 g, 25.4 mmol) to a solution of 4-hydroxyacetophenone (3.0 g, 22.1 mmol) in 30 mL dimethylsulfoxide. After fifteen minutes, 1-phenylethyl bromide (5.1 g, 27.6 mmol) was added and the mixture was stirred for an additional sixty minutes. The reaction mixture was poured into 100 mL of water and extracted with tether. The ether solution was dried over anhydrous magnesium sulfate and the ether evaporated to yield the product which was used without further purification.

b) 1-(4-(1-phenylethoxy)phenyl)ethyl acetophenone oxime was prepared by dissolving the product of Example 1a above (4.2 g, 17.5 mmol) and 4.2 g (60.4 mmol) of hydroxylamine hydrochloride in a mixture of 30 mL of ethanol and 30 mL of pyridine. The solution was heated at 50° C. for two hours. At the end of this time, most of the solvent was removed under vacuum and the residue was taken up in ether. After washing with 50 mL of 2N HCl, the solution was dried over anhydrous magnesium sulfate and evaporated. The produce was a thick oily residue which was used without further purification.

c) 1-(4-(1-phenylethoxy)phenyl)ethyl hydroxylamine was prepared by dissolving the product of Example 1b above (4.3 g, 16.9 mmol) in 80 mL of ethanol and first cooling the mixture to 0° C. Borane/pyridine complex (4.5 g, 50.7 mmol) was added via syringe under nitrogen, followed ten minutes later by 17 mL of 6N HCl. Within thirty minutes, the reaction was complete. and the reaction mixture was brought to pH 9 by the addition of solid sodium carbonate. The mixture was extracted into ether and dried over anhydrous magnesium sulfate. Evaporation of the ether yielded the title compound as a yellow oil which was used without further purification.

d) N-hydroxy-N-(1-(4-(1-phenylethoxy)phenyl)-ethyl]urea was prepared by heating a mixture of 2.22 g (8.64 mmol) of 1-(4-(1-phenylethoxy)phenyl)ethyl hydroxylamine and 1.19 g (10.4 mmol) of trimethylisocyanate in 30 mL of dioxane under reflux for thirty minutes. The reaction mixture was then washed with saturated aqueous ammonium chloride solution, dried over anhydrous magnesium sulfate, and evaporated. The residue was washed with ether to give 1.3 g of the desired product as a white solid.

Alternatively, the title compound was prepared by dissolving the product of Example 1(c) in toluene and bubbling hydrogen chloride gas through the mixture at a moderate rate for about four minutes. The mixture was then heated under reflux for one hour, cooled to room temperature, and then treated with an excess of cold aqueous ammonia solution. The precipitate was collected by filtration and recrystallized from aqueous ethanol to produce the title compound, mp 125°–130° C.

NMR (300 MHz. DMSO—$d_6$): 1.53 (d. 3H); 1.82 (d, 3H); 5.19 (q, 1H); 5.95 (q, 1H); 6.23 (brs, 2H); 6.81 (m, 2H); 7.15 (m, 2H); 7.22–7.43 (m, 5H); 8.95 (brs, 1H).

Mass spectrum (CI—NH₃): 301 (M=1)⁺, 283, 240, 225, 121.

EXAMPLE 2

Preparation of N-hydroxy-N-[1-(4-(1-phenylethoxy)-3,5-dimethoxyphenyl)ethyl]urea The title compound was prepared according to the procedure of Example 1 substituting 3,5-dimethoxy-4-hydroxyacetophenone for 4-hydroxyacetophenone. It was necessary to reflux the alkylation reaction with 1-phenylethylbromide for 3 days. m.p.=129°–132° C.; ¹H NMR (300 MHz, DMSO—d₆): 1.36 (3H, d, J=6.9 Hz), 1.41 (3H, d, J=6.6 Hz), 3.71 (6H, s), 5.16–5.28 (2H, m), 6.35 (2H, s), 6.59 (2H, s), 7.20–7.35 (3H, m), 7.41–7.47 (2H, m), 9.03 (1H, s); MS, (M+H)⁺=361, (M+NH₄)=378; Analysis calc'd for C₁₉H₂₄N₂O₅: C, 63.32; H, 6.71; N, 7.77; Found: C, 62.90; H, 6.86; N, 7.69.

EXAMPLE 3

Preparation of N-hydroxy-N-[1-(4-(1-phenylethoxy)-3-methylphenyl)ethyl]urea;

The title compound was prepared according to the procedure of Example 1, substituting 4-hydroxy-3-methylacetophenone for 4-hydroxyacetophenone. m.p.=133°–135° C.; ¹H NMR (500 MHz, DMSO—d₆): 1.31 (3H, d, J=7.0 Hz), 1.54 (3H, d, J=6.3 Hz), 2.21 (3H, s), 5.15 (1H, q, 7.0 Hz), 5.45 (1H, q, J=6.3 Hz), 6.16 (2H, s), 6.70 (1H, d, J=8.5 Hz), 6.95 (1H, d, J=8.5 Hz), 7.08 (1H, s), 7.23 (1H, t, 7.5 Hz), 7.33 (2H, t, 7.5 Hz), 7.40 (2H, d, 7.5 Hz), 8.88 (1H, d, J=2.0 Hz); MS, FAB (M+H)⁺=315, (M+Na)⁺=337; Analysis calc'd for C₁₈H₂₂N₂O₃: C, 68.77; H, 7.05; N, 8.91; Found: C, 68.80; H, 7.07; N, 8.95.

EXAMPLE 4

Preparation of N-hydroxy-N-[1-(4-(1-phenylethoxy)-2-methylphenyl)ethyl]urea

The title compound was prepared according to the procedure of Example 1, substituting 4-hydroxy-2-methylacetophenone for 4-hydroxyacetophenone. M.p.=157°–158° C.; ¹H NMR (300 MHz, DMSO—d₆): 1.27 (3H, d, J=7.0 Hz), 1.52 (3H, d, J=6.6 Hz), 2.22 (3H, s), 5.35 (1H, q, 7.0 Hz), 5.44 (1H, q, J=6.6 Hz), 6.17 (2H, s), 6.63–6.71 (2H, m), 7.20–7.42 (6H, m), 8.88 (1H, s); MS (M+H)⁺=315, (M+NH₄)⁺=332; Analysis calc'd for C₁₈H₂₂N₂O₃: C, 68.77; H, 7.05; N, 8.91; Found: C, 68.79; H, 7.04; N, 8.94.

EXAMPLE 5

Preparation of N-hydroxy-N-[1-(4-(1-phenylethoxy)-2-hydroxyphenyl)ethyl]urea To a stirred solution of 2,4-dihydroxyacetophenone (10.0 g, 65.7 mmol) in acetone (200 mL) at room temperature was added potassium carbonate (9.0 g, 66 mmol) followed by 1-phenylethylbromide (7.9 g, 66 mmol). The mixture was refluxed for 20 hrs and cooled to room temperature. The mixture was concentrated to one-half volume, diluted with water and extracted with ethyl acetate (3×300 mL). The combined extract was washed with saturated aqueous NaCl, dried with MgSO₄, and concentrated. The crude product was twice recrystallized, first in warm hexane then in ether, cooled to −20° C. to afford 4-(1-phenylethoxy)-2-hydroxyacetophenone. m.p.=78°–80° C.

To a stirred solution of the 4-(1-phenylethoxy)-2-hydroxyacetophenone obtained above (25.1 g, 97.9 mmol) in ethanol (300 mL) and pyridine (100 mL) at room temperature was added hydroxylamine hydrochloride (13.6 g, 196 mmol). Stirred at room temperature for 20 hrs. Concentrated reaction mixture to approximately 100 mL and the resulting concentrated solution diluted with 1N HCl. Extracted mixture with ether (3×400 mL). Combined ether extracts were dried with MgSO₄, concentrated, and codistilled with toluene (2×300 mL). Crude product was recrystallized in ether-hexane, cooled to −20° C., to afford 18.58 g oxime intermediate (70%). m.p.=79°–81° C.

To a stirred solution of oxime (3.4 g, 12.5 mmol) in ethanol (100 mL) was added borane-pyridine complex (5.09 mL, 50.4 mmol) dropwise. The solution was stirred 0.5 hr at room temperature. To this solution, placed in a room temperature water bath, was added 2N HCl (150 mL) dropwise via dropping funnel (1 drop/sec). After addition complete, reaction mixture stirred an additional 1 hr. Reaction mixture was then cooled to 0° C. and neutralized with 6N NaOH. Extracted neutralized mixture with ether (4×500 mL). Combined ether extracts were washed with saturated NaCl aqueous solution, dried with MgSO₄, and concentrated to afford 3.2 g crude product. Flash chromatography on 120 g silica gel using dichloromethane/2% methanol as eluent afforded 1.90 g white foam, hydroxylamine intermediate (56%).

To a stirred solution of hydroxylamine (1.90 g, 7.0 mmol) in THF (100 mL) at room temperature was added trimethylsilylisocyanate (1.16 mL, 85%, 7.3 mmol) dropwise via syringe. Stirred reaction mixture 20 hrs at room temperature. Added water (0.5 mL, 27 mmol) to quench reaction and concentrated to a viscous oil. Chromatography on 100 g silica gel using dichloromethane/2.5% methanol as eluent afforded 1.73 g of the desired hydroxyurea (78%) as a glass. ¹H NMR (300 MHz, DMSO—d₆): 1.29 (3H, d, J=7.0 Hz), 1.50 (3H, d, J=6.3 Hz), 5.30–5.40 (2H, m), 6.27–6.38 (4H, m), 7.08–7.40 (6H, m), 9.12 (1H, d, J=1.5 Hz), 9.48 (1H, d, J=3.0 Hz); MS, (M+H)⁺=317, (M+NH₄)=334; Analysis calc'd for C₁₇H₂₀N₂O₄: C, 64.54; H, 6.37; N, 8.85; Found: C, 64.32; H, 6.45; N, 8.72.

EXAMPLE 6

Preparation of N-hydroxy-N-[1-(4-(-phenylethoxy)-3-methoxyphenyl)ethyl]urea

The title compound was prepared according to the procedure of Example 1, substituting 4-hydroxy-3-methoxyacetophenone for 4-hydroxyacetophenone. m.p.=112°–115° C.; ¹H NMR (300 MHz, DMSO—d₆): 1.32 (3H, d, J=6.9 Hz), 1.52 (3H, d, J=6.6 Hz), 3.77 (3H, s), 5.17 (1H, q, J=6.9 Hz), 5.40 (1H, q, J=6.6 Hz), 6.26 (2H, s), 6.65–6.74 (2H, m), 6.91 (1H, s), 7.20–7.42 (5H, m), 8.95 (H, s); MS (M+H)⁻=331, (M+NH₄)=348; Analysis calc'd for C₁₈H₂₂N₂O₄: C, 65.44; H, 6.71; N, 8.48; Found C, 65.09; H, 7.08; N, 8.41.

EXAMPLE 7

Preparation of
N-hydroxy-N-[1-(4-(1-(2-methylphenyl)-ethoxy)-phenyl)ethyl]urea

The title compound was prepared according to the procedure of Example 1 substituting 1-(2-methylphenyl)ethylbromide (J. Org. Chem. 1972, 37, 2343) for 1-phenylethylbromide. $^1$H NMR (300 MHz, DMSO—$d_6$): 1.32 (3H, d, J=7.2 Hz), 1.51 (3H, d, J=6.6 Hz), 2.38 (3H, s), 5.18 (1H, q, J=7.2 Hz), 5.54 (1H, q, J=6.6 Hz), 6.22 (2H, s), 6.70-6.76 (2H, m), 7.10-7.19 (5H, m), 7.30-7.37 (1H, m), 8.93 (1H, d, J=2.1 Hz); MS (M+H)$^+$=315, (M+NH$_4$)$^+$=332; Analysis calc'd for $C_{18}H_{22}N_2O_3$: C, 68.77; H, 7.05; N, 8.91; Found: C, 69.28; H, 7.81; N, 8.91.

EXAMPLE 8

Preparation of
N-hydroxy-N-[1-(4-(1-phenylethoxy)phenyl)-ethyl]-N'-methylurea

The title compound was prepared according to the procedure of Example 1 using methylisocyanate instead of trimethylsilylisocyanate.

EXAMPLE 9

Preparation of
N-hydroxy-N-[1-(4-(1-phenylethoxy)phenyl)-ethyl]-N'-propylurea

The title compound was prepared according to the procedure of Example 1 using propylisocyanate instead of trimethylsilylisocyanate.

EXAMPLE 10

Preparation of
N-hydroxy-N-[1-(4-(1-phenylethoxy)phenyl)-2-methylpropyl]urea

The title compound was prepared according to the procedure of Example 1 using 1-(4-hydroxyphenyl)-2-methylpropanone instead of 4-hydroxyphenylacetophenone.

EXAMPLE 11

Preparation of
N-hydroxy-N-[1-(4-(1-phenylethoxy)phenyl)-butyl]urea

The title compound was prepared according to the procedure of Example 1 using 4-hydroxyphenylbutyrophenone instead of 4-hydroxyphenylacetophenone.

EXAMPLE 12

Preparation of
N-hydroxy-N-[1-(4-(1-phenylethoxy)-2-methoxyphenyl)ethyl]urea

The title compound was prepared according to the procedure of Example 1 using 4-hydroxy-2-methoxyacetophenone instead of 4-hydroxyphenylacetophenone.

EXAMPLE 13

Preparation of
N-hydroxy-N-[1-(4-(1-phenylethoxy)-2-hydroxy-3-methylphenyl)ethyl]urea The title compound was prepared according to the procedure of Example 1 using 2,4-dihydroxy-3-methylacetophenone instead of 4-hydroxyphenylacetophenone.

EXAMPLE 14

Preparation of
N-hydroxy-N-[1-(4-(1-phenylethoxy)-3,5-dimethylphenyl)ethyl]urea

The title compound was prepared according to the procedure of Example 1 using 4-hydroxy-3,5-dimethylacetophenone instead of 4-hydroxyphenylacetophenone.

EXAMPLE 15

Preparation of
N-hydroxy-N-[1-(4-(1-phenylethoxy)-3-chlorophenyl)ethyl]urea

The title compound was prepared according to the procedure of Example 1 using 4-hydroxy-3-chloroacetophenone instead of 4-hydroxyphenylacetophenone.

EXAMPLE 16

Preparation of
N-hydroxy-N-[1-(4-(1-phenylethoxy)-2-isopropyloxyphenyl)ethyl]urea The title compound was prepared according to the procedure of Example 1 using 4-hydroxy-2-isopropyloxyacetophenone instead of 4-hydroxyphenylacetophenone.

EXAMPLE 17

Preparation of
N-hydroxy-N-[1-(4-(1-phenylethoxy)-3-cyanophenyl)ethyl]urea

The title compound was prepared according to the procedure of Example 1 using 4-hydroxy-3-cyanoacetophenone instead of 4-hydroxyphenylacetophenone.

EXAMPLE 18

Preparation of
N-hydroxy-N-[1-(4-(1-(4-fluorophenyl)ethoxy)-3-cyanophenyl)ethyl]urea The title compound was prepared according to the procedure of Example 1 using 4-hydroxy-3-cyanoacetophenone instead of 4-hydroxyphenylacetophenone and 1-(4-fluorophenyl)ethylbromide instead of 1-phenylethylbromide.

EXAMPLE 19

N-hydroxy-N-[1-(4-(1-phenylethoxy)-3,5-dichlorophenyl)ethyl]urea

The title compound was prepared according to the procedure of Example 1 using 4-hydroxy-3,5-dichloroacetophenone instead of 4-hydroxyphenylacetophenone.

EXAMPLE 20

Preparation of
N-hydroxy-N-[1-(4-(1-(4-fluorophenyl)ethoxy)-3,-fluorophenyl)ethyl]urea The title compound was prepared according to the procedure of Example 1 using 4-hydroxy-3-fluoroacetophenone instead of 4-hydroxyphenylacetophenone and 1-(4-fluorophenyl)ethylbromide instead of 1-phenylethylbromide.

EXAMPLE 21

Preparation of N-hydroxy-N-1-(4-(1-(4-ethylphenyl)ethoxy)-3-fluorophenyl)ethyl]urea The title compound was prepared according to the procedure of Example 1 using 4-hydroxy-3-fluoroacetophenone instead of 4-hydroxyphenylacetophenone and 1-(4-ethylphenyl)ethylbromide instead of 1-phenylethylbromide.

EXAMPLE 22

Preparation of N-hydroxy-N-[1-(4-1-(4-fluorophenyl)ethoxy)-2-hydroxy-3-methylphenyl)ethyl]urea The title compound was prepared according to the procedure of Example 1 using 2,4-dihydroxy-3-methylacetophenone instead of 4-hydroxyphenylacetophenone and 1-(4-fluorophenyl)ethyl bromide instead of 1-phenylethylbromide.

EXAMPLE 23

Preparation of N-hydroxy-N-1-(4-(1-(4-cyanophenyl)ethoxy)-phenyl)ethyl]urea

The title compound was prepared according to the procedure of Example 2 using 1-(4-cyanophenyl)ethyl bromide instead of 1-phenylethylbromide.

EXAMPLE 24

Preparation of N-hydroxy-N-1-(4-(1-(4-trifluoromethyl)-phenyl)ethoxy)-3-methylphenyl)ethyl]urea The title compound was prepared according to the procedure of Example 1 using 4-hydroxy-3-methylacetophenone instead of 4-hydroxyphenylacetophenone and 1-(trifluoromethylphenyl)ethyl bromide instead of 1-phenylethylbromide.

EXAMPLE 25

Preparation of N-hydroxy-N-1-(4-(1-(4-methoxy-3-fluorophenyl)ethoxy)phenyl)ethyl]urea The title compound was prepared according to the procedure of Example 1 using 1-(3-fluoro-4-methoxyphenyl)ethyl bromide instead of 1-phenylethylbromide.

EXAMPLE 26

Preparation of N-hydroxy-N-1-(4-(1-(4-methylmercaptophenyl)ethoxy)phenyl)ethyl]urea The title compound was prepared according to the procedure of Example 1 using 1-(4-methylmercaptophenyl)ethyl bromide instead of 1-phenylethylbromide.

EXAMPLE 27

Preparation of N-hydroxy-N-1-(4-(1-(3-chlorophenyl)ethoxy)-3-methylphenyl)ethyl]urea The title compound was prepared according to the procedure of Example 1 using 4-hydroxy-3-methylacetophenone instead of 4-hydroxyphenylacetophenone and 1-(3-chlorophenyl)ethyl bromide instead of 1-phenylethylbromide.

EXAMPLE 28

Preparation of N-hydroxy-N-1-(4-(1-(2-chlorophenyl)ethoxy)-3-methylphenyl)ethyl]urea The title compound was prepared according to the procedure of Example 1 using 4-hydroxy-3-methylacetophenone instead of 4-hydroxyphenylacetophenone and 1-(2-chlorophenyl)ethyl bromide instead of 1-phenylethylbromide.

EXAMPLE 29

Preparation of N-hydroxy-N-1-(4-(1-(4-propylphenyl)ethoxy)-3-methylphenyl)ethyl]urea The title compound was prepared according to the procedure of Example 1 using 4-hydroxy-3-methylacetophenone instead of 4-hydroxyphenylacetophenone and 1-(4-propylphenyl)ethyl bromide instead of 1-phenylethylbromide.

EXAMPLE 30

Preparation of N-hydroxy-N-[1-(4-(1-(4-propylphenyl)ethoxy)-phenyl)ethyl]urea

The title compound was prepared according to the procedure of Example 1 using 1-(4-propylphenyl)ethyl bromide instead of 1-phenylethylbromide.

EXAMPLE 31

Preparation of N-hydroxy-N-[1-(4-(1-(4-fluorophenyl)ethoxy)-phenyl)ethyl]urea a) 1-(4-Fluorophenyl)ethanol was prepared by mixing 10 g (72 mmol) of 4-fluorophenylacetophenone and 2.74 g (72 mmol) of sodium borohydride in 100 mL of ethanol. After one hour the solvent was removed under vacuum and the residue was taken up in diethyl ether. The ether solution was dried over anhydrous magnesium sulfate and evaporated to yield the crude product which was used without further purification.

b) 1-(4-Fluorophenyl)-1-bromoethane was prepared by dissolving 20.75 g (79 mmol) of triphenyl phosphine in 100 mL of dichloromethane and adding 12.68 g (79 mmol) of bromine. To this mixture was added 10.1 g of the crude product prepared in Example 31(a) above. The triphenylphosphine oxide which formed was removed by filtration and the solvent was evaporated under vacuum to yield crude 1-(4-fluorophenyl)-1-bromoethane which was used without further purification.

c) 4-(1-(4-Fluorophenyl)ethoxy)acetophenone was prepared using the method described in Example 1(a) above, but using as the starting material the product of Example 31(b).

d) N-hydroxy-N-(1-(4-(1-(4-fluorophenyl)ethoxy)-phenyl)ethyl]hydroxylamine was prepared according the method detailed above in Example 1. parts b-c. except that the starting material was 4-(1-(4-fluorophenyl)ethoxy)-acetophenone. prepared in Example 31(c) above rather than 1-(4-(1-phenylethoxy)phenyl)ethyl acetophenone.

e) N-Hydroxy-N-(1-(4-(1-(4-fluorophenyl)ethoxy)-phenyl)ethyl]acetamide was prepared by the reaction of the hydroxylamine compound prepared in step (d) above with two equivalents of acetyl chloride in the presence of triethylamine in THF. The intermediate N,O-diacetyl compound was extracted with ethyl acetate, dried over anhydrous magnesium sulfate, after which the solvent was evaporated. The residue was taken up in isopropyl alcohol and a solution of lithium hydroxide in water was added. The mixture was stirred until the reaction was complete, and then neutralized by the addition of 2N HCl. This mixture was extracted with ether, the ether solution dried over anhydrous magnesium sulfate, and evaporated to yield the title compound.

NMR (300 MHz, DMSO—$d_6$): 1.36 (d, 3H); 1.51 (d, 3H); 5.50 (m, 2H); 6.82 (m, 2H); 7.15 (m, 4H); 7.45 (m, 2H); 9.48 (brs, 1H).

Mass spectrum (CI—$NH_3$): 335 (M+NH)$^+$, 318, (M+1)$^+$, 302, 274, 243, 198.

EXAMPLE 32

Preparation of
N-hydroxy-N-1-(4-(1-(4-fluorphenyl)ethoxy)-phenyl)ethyl]urea

N-Hydroxy-N-[1-(4-(1-(4-fluorophenyl)-ethoxy)ethyl]urea was prepared by reacting 1-(4-(1-(4-fluorophenyl)ethoxy)phenyl)ethyl hydroxylamine, prepared in Example 31 above with trimethylsilyl isocyanate using the method described in Example 1(d) above.

NMR (300 MHz, DMSO—$d_6$): 1.32 (d, 3H); 1.53 (d, 3H); 5.49 (m, 2H); 6.23 (s, 2H); 6.82 (m, 2H); 7.17 (m, 4H); 7.45 (m, 2H); 8.97 (brs, 1H).

Mass spectrum (EI): 318$^+$, 301, 243.

EXAMPLE 33

Preparation of
N-hydroxy-N-1-(4-(1-4-chlorophenyl)-ethoxy)phenyl)ethyl]acetamide The title compound was prepared according to the method of Example 31 above, except using 4-chloroacetophenone in place of 4-fluoroacetophenone.

NMR (300 MHz, DMSO—$d_6$): 1.36 (d, 3H); 1.52 (d,3H); 96 (s, 3H); 5.50 (m, 2H); 6.83, d, 2H); 7.14 (d, 2H); 7.42 (m, 4H); 9.46 (brs, 1H).

Mass spectrum (CI): 334, 316, 259, 139, 121.

EXAMPLE 34

Preparation of
N-hydroxy-N-[1-(4-(1-(4-chlorophenyl)ethoxy)-phenyl)ethyl]urea

The title compound was prepared according to the method of Example 32 above, except substituting 4-chloroacetophenone in place of 4-fluoroacetophenone.

NMR (300 MHz, CDCl$_3$): 1.47 (d, 3H); 1.60 (d, 3H);, 5.14 (brs, 2H); 5.26 (q, 1H); 5.38 (q, 1H); 6.20 (brd, 1H); 6 79 (d, 2H); 7.30 (m, 4H).

Mass spectrum (EI): No M$^+$, 317, 259, 139, 121, 103.

DETERMINATION OF PLASMA HALF-LIFE

Rats were injected intravenously with a 1.7 mL/kg solution of test compound through a jugular cannula. Multiple blood samples were collected from the lateral tail vein using heparinized capillary tubes. Plasma was obtained by centrifugation and precipitation of proteins by 2 volumes of methanol was followed by centrifugation at 12000×G for 10 min. The supernatant was analyzed by HPLC using a $C_{18}$ Adsorbosphere 7μm column and eluted with a mobile phase of varying amounts of acetonitrile and aqueous 8mM triethylamine acetate and 10mM acetohydroxamic acid with a flow rate of about 1mL/min and detection by UV spectroscopy. The quantitation of compounds was calculated using external standards. The halflife of a test compound was determined from the elimination phase of a graph of the log of the plasma concentration versus time.

The data presented in Table 1 shows the 5-lipoxygenase inhibitory activity and the plasma halflives of representative compounds of the present invention in which $R_2$ is methyl compared with data for compounds in which $R_2$ is hydrogen, as disclosed and claimed in U.S. Pat. No. 4,738,986. Both sets of compounds demonstrate potent in vitro inhibition of 5-lipoxygenase. However, significant improvements in the plasma lifetimes are observed for the compounds of the present invention when compared with those of the prior art. Increased duration of action for 5-lipoxygenase inhibitors is beneficial for treating chronic diseases associated with abnormal levels of leukotriene mediators. Longer plasma halflives provide for less frequent dosing of host organisms in need of such treatment.

SYNTHESIS OF COMPARATIVE EXAMPLES

Examples A through F represent prior art compounds in which $R_2$ is hydrogen, used for the comparative data presented in Table 1, and were prepared in a manner analogous to the preparation of the corresponding compounds of the present invention where R2 is methyl, except the starting material in each case was the appropriate benzylbromide instead of the corresponding phenylethylbromide.

TABLE 1

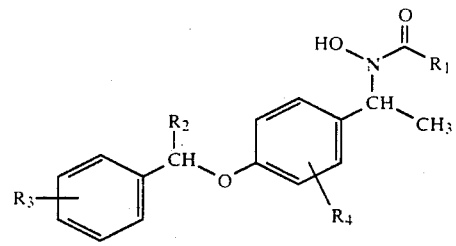

| Example | R$_1$ | R$_2$ | R$_3$ | R$_4$ | 5-Lipoxygenase Inhibitory Activity IC50 (Micromolar) | Plasma Halflife (Hours) |
|---|---|---|---|---|---|---|
| 3 | NH$_2$ | CH$_3$ | H | 3-CH$_3$ | 0.2 | 5.3 |
| A* | NH$_2$ | H | H | 3-CH$_3$ | 0.1 | 2.7 |
| 4 | NH$_2$ | CH$_3$ | H | 2-CH$_3$ | 0.05 | 1.2 |
| B* | NH$_2$ | H | H | 2-CH$_3$ | 0.4 | 0.6 |
| 31 | CH$_3$ | CH$_3$ | 4-F | H | 0.5 | 12.4 |
| C* | CH$_3$ | H | 4-F | H | 0.5 | 5.6 |
| 32 | NH$_2$ | CH$_3$ | 4-F | H | 0.3 | 7.2 |
| D* | NH$_2$ | H | 4-F | H | 0.4 | biphasic |
| 33 | CH$_3$ | CH$_3$ | 4-Cl | H | 0.6 | 5.7 |
| E* | CH$_3$ | H | 4-Cl | H | 91% (0.78 μM) | 1.4 |
| 34 | NH$_2$ | CH$_3$ | 4-Cl | H | 0.2 | 7.8 |
| F* | NH$_2$ | H | 4-Cl | H | 72% (0.39 μM) | 4.6 |

*Prior art compounds

We claim:
1. A compound having the formula

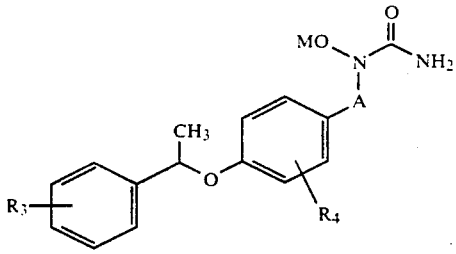

wherein
  A is straight or branched divalent alkylene of from one to four carbon atoms;
  $R_3$ is one or more substituents selected from
    hydrogen,
    alkyl of from one to six carbon atoms,
    alkoxy of from one to six carbon atoms,
    thioalkoxy of from one to six carbon atoms,
    halogen,
    cyano, and
    trihalomethyl;
  $R_4$ is one or more substituents selected from
    hydrogen,
    alkyl of from one to six carbon atoms,
    alkoxy of from one to six carbon atoms,
    thioalkoxy of from one to six carbon atoms,
    hydroxy,
    halogen,
    cyano, and
    trihalomethyl; and
  M is
    hydrogen,
    a pharmaceutically acceptable cation, or
    a metabolically cleavable group selected from the group consisting of
      formyl,
      acetyl,
      benzoyl,
      methoxycarbonyl,
      ethoxycarbonyl,
      tert-butylcarbonyl
      glutaryl,
      succinyl, and
      carbamoyl;
  with the proviso that when A is >CHCH$_3$, $R_3$ and $R_4$ may not both be hydrogen.

2. A compound as defined by claim 1 wherein A is >CHCH$_3$.

3. A compound as defined by claim 1 wherein R3 and R4 are independently selected from alkyl of from one to six carbon atoms.

4. A pharmaceutical composition for use in inhibiting 5-and 12-lipoxygenase comprising a lipoxygenase inhibiting effective amount of a compound as defined by claim 1 in combination with a pharmaceutically acceptable carrier.

5. A method of inhibiting 5- or 12- lipoxygenase activity in a host mammal in need of such treatment comprising administering a pharmaceutical composition as defined by claim 4.

6. A compound as defined in claim 1 selected from the group consisting of:
N-hydroxy-N-[1-(4-(1-(2-methylphenyl)phenyl)ethyl]urea;
N-hydroxy-N-[1-(4-(1-phenylethoxy)-3-methylphenyl)ethyl]urea;
N-hydroxy-N-[1-(4-(1-phenylethoxy)-2-methylphenyl)ethyl]urea;
N-hydroxy-N-[1-(4-(1-(4-propylphenyl)ethoxy)-3-methylphenyl)ethyl]urea;
N-hydroxy-N-[1-(4-(1-(4-propylphenyl)ethoxy)-phenyl)ethyl]urea;
N-hydroxy-N-[1-(4-(1-phenylethoxy)-3,5-dimethylphenyl)ethyl]urea;
N-hydroxy-N-[1-(4-(1-phenylethoxy)phenyl)-2-methylpropyl)]urea;
N-hydroxy-N-[1-(4-(1-phenylethoxy)-2-iso-propyloxyphenyl)ethyl]urea;
N-hydroxy-N-[1-(4-(1-phenylethoxy)phenyl)butyl]urea;
N-hydroxy-N-[1-(4-(1-phenylethoxy)phenyl)-2-hydroxyphenyl)ethyl]urea;
N-hydroxy-N-[1-(4-(1-phenylethoxy)-2-hydroxy-3-methylphenyl)ethyl]urea;
N-hydroxy-N-[1-(4-(1(4-methoxy-3-fluorophenyl)ethoxy)phenyl)ethyl]urea;
N-hydroxy-N-[1-(4-(1-phenylethoxy)-2-methoxyphenyl)ethyl]urea;
N-hydroxy-N-[1-(4-(1-phenylethoxy)-3-methoxyphenyl)ethyl]urea;
N-hydroxy-N-[1-(4-(1-phenylethoxy)-3,5-dimethoxyphenyl)ethyl]urea;
N-hydroxy-N-[1-(4-(1(4-methylmercaptophenyl)ethoxy)phenyl)ethyl]urea;
N-hydroxy-N-[1-(4-(1-(2-chlorophenyl)ethoxy)-3-methylphenyl)ethyl]urea;
N-hydroxy-N-[1-(4-(1-(3-chlorophenyl)ethoxy)-3-methylphenyl)ethyl]urea;
N-hydroxy-N-[1-(4-(1-(4-fluorophenyl)ethoxy)phenyl)ethyl]urea;
N-hydroxy-N-[1-(4-(1-(4-chlorophenyl)ethoxy)phenyl)ethyl]urea;
N-hydroxy-N-[1-(4-(1-(4-chlorophenyl)ethoxy)-3-fluorophenyl)ethyl]urea;
N-hydroxy-N-[1-(4-(1-(4-chlorophenyl)ethoxy)-3-cyanophenyl)ethyl]urea;
N-hydroxy-N-[1-(4-(1-(4-chlorophenyl)ethoxy)-2-hydroxy-3-methylphenyl)ethyl]urea;
N-hydroxy-N-[1-(4-(1-(4-cyanophenyl)ethoxy)phenyl)ethyl]urea;
N-hydroxy-N-[1-(4-(1-(4-trifluorophenyl)ethoxy)-3-methylphenyl)ethyl]urea;
N-hydroxy-N-[1-(4-(1-phenylethoxy)-3-chlorophenyl)ethyl]urea;
N-hydroxy-N-[1-(4-(1-(4-ethylphenyl)ethoxy)-3-fluorophenyl)ethyl]urea;
N-hydroxy-N-[1-(4-(1-phenylethoxy)-3-cyanophenyl)ethyl]urea;
N-hydroxy-N-[1-(4-(1-phenylethoxy)-3,5-dichlorophenyl)ethyl]urea; or
a pharmaceutically acceptable salt thereof.

* * * * *

UNITED STATES PATENT AND TRADEMARK OFFICE
CERTIFICATE OF CORRECTION

PATENT NO. : 5,026,729  Page 1 of 2

DATED : June 25, 1991

INVENTOR(S) : DEE W. BROOKS; JAMES B. SUMMERS; JAMES H. HOLMS.

It is certified that error appears in the above-identified patent and that said Letters Patent is hereby corrected as shown below:

Column 1, line 51: Replace "Lioid" with --Lipid--.

Column 4, lines 25-26: Replace "N-hydroxy-N-[!-(4-(1-phenylethoxy)-2-iso-propyloxyphenyl)-ethyl]urea"
with --"N-hydroxy-N-[1-(4-(1-phenylethoxy)-2-iso-propyloxyphenyl)-ethyl]urea--.

Column 4, line 45: Replace "N-hydroxy-N-[1-(4ethoxy)phenyl)[ethyl]urea"
with --N-hydroxy-N-[1-(4-(1-(4-methylmercaptophenyl)ethoxy)-phenyl)[ethyl]urea--.

Column 20, lines 3-4: Replace "N-hydroxy-N-[1-(4-(1-(2-methylphenyl)phenyl)ethyl]urea" with
--N-hydroxy-N-[1-(4-(1-(2-methylphenyl)ethoxy)phenyl)ethyl]urea--.

Column 20, lines 34-35: Replace "N-hydroxy-N-[1-(4-(1(4-methylmercaptophenyl)ethoxy)-phenyl)ethyl]urea with
--N-hydroxy-N-[1-(4-(1-(4-methylmercaptophenyl)ethoxy)-phenyl)ethyl]urea--.

UNITED STATES PATENT AND TRADEMARK OFFICE
CERTIFICATE OF CORRECTION

PATENT NO. : 5,026,729

DATED : June 25, 1991

INVENTOR(S) : DEE W. BROOKS; JAMES B. SUMMERS; JAMES H. HOLMS.

It is certified that error appears in the above-identified patent and that said Letters Patent is hereby corrected as shown below:

Column 4, Line 56: Replace "(4-fluorphenyl) with --(4-fluorophenyl)--.

Column 10, line 18: Replace "tether" with --ether--.

Signed and Sealed this

Twenty-fifth Day of May, 1993

Attest:

MICHAEL K. KIRK

*Attesting Officer*     Acting Commissioner of Patents and Trademarks